US010395557B2

(12) United States Patent
Lecat

(10) Patent No.: US 10,395,557 B2
(45) Date of Patent: *Aug. 27, 2019

(54) METHOD AND APPARATUS FOR AUSCULTATION TRAINING

(71) Applicant: Paul Jacques Charles Lecat, Tallmadge, OH (US)

(72) Inventor: Paul Jacques Charles Lecat, Tallmadge, OH (US)

(*) Notice: Subject to any disclaimer, the term of this patent is extended or adjusted under 35 U.S.C. 154(b) by 161 days.

This patent is subject to a terminal disclaimer.

(21) Appl. No.: 15/429,957

(22) Filed: Feb. 10, 2017

(65) Prior Publication Data

US 2017/0243521 A1 Aug. 24, 2017

Related U.S. Application Data

(60) Provisional application No. 62/296,855, filed on Feb. 18, 2016, provisional application No. 62/308,254, filed on Mar. 15, 2016.

(51) Int. Cl.
*G09B 23/28* (2006.01)
*A61B 7/02* (2006.01)
(Continued)

(52) U.S. Cl.
CPC ............... *G09B 23/28* (2013.01); *A61B 7/02* (2013.01); *G09B 5/04* (2013.01); *H04R 1/46* (2013.01);
(Continued)

(58) Field of Classification Search
CPC ...... H04R 1/46; H04R 27/00; H04R 2420/07; G09B 23/28; G09B 23/285; G09B 5/04; A61B 7/02
(Continued)

(56) References Cited

U.S. PATENT DOCUMENTS 2,385,221 A * 9/1945 Minsky ............... A61B 7/04
381/67
3,947,974 A 4/1976 Gordon et al.
(Continued)

FOREIGN PATENT DOCUMENTS

JP 09 146 452 6/1997
JP 2005 077 521 3/2005
(Continued)

OTHER PUBLICATIONS

3M, "Littmann Electronic Stethoscope," Website, Date Unknown, http://www.3m.com/3M/en_US/company-us/all-3m-products/~/3M-Littmann-Electronic-Stethoscope-Model-3200?N=5002385+87077 95+8707798+8711017+8711096+8711500+8711724+8727094+329 3188392&rt=rud.
(Continued)

*Primary Examiner* — Samchuan C Yao
*Assistant Examiner* — Lily M Del Valle
(74) *Attorney, Agent, or Firm* — Emerson, Thomson & Bennett, LLC; Roger D. Emerson

(57) ABSTRACT

Provided is an auscultation training device having a stethoscope with a headpiece; at least one earpiece; tubing, wherein the tubing has a generally hollow interior; a speaker inserted into the hollow interior of the tubing, further having a 3.5 mm audio jack wherein the insertion points of the speaker forms an airtight seal with the tubing, and wherein the speaker does not obstruct the hollow interior of the tubing. Further provided is a method for auscultation training using the disclosed device.

25 Claims, 5 Drawing Sheets

(51) Int. Cl.
  *G09B 5/04* (2006.01)
  *H04R 1/46* (2006.01)
  *H04R 27/00* (2006.01)
  *A61B 7/04* (2006.01)

(52) U.S. Cl.
  CPC .............. *H04R 27/00* (2013.01); *A61B 7/04* (2013.01); *H04R 2420/07* (2013.01)

(58) Field of Classification Search
  USPC ........................................................ 434/262
  See application file for complete search history.

(56) References Cited

U.S. PATENT DOCUMENTS

| | | | |
|---|---|---|---|
| 3,989,895 A * | 11/1976 | O'Daniel, Sr. | A61B 7/026 600/528 |
| 4,155,196 A * | 5/1979 | Bollinger | A63H 33/3094 446/130 |
| 4,770,189 A | 9/1988 | Shyu | |
| 4,783,813 A * | 11/1988 | Kempka | A61B 7/04 381/67 |
| 5,774,563 A | 6/1998 | DesLauriers et al. | |
| 6,220,866 B1 | 4/2001 | Amend et al. | |
| 6,503,087 B1 | 1/2003 | Eggert et al. | |
| 6,527,559 B2 | 3/2003 | Yoshii et al. | |
| 7,115,102 B2 | 10/2006 | Abbruscato | |
| 7,209,796 B2 | 4/2007 | McKinney et al. | |
| 7,645,141 B2 | 1/2010 | Lecat | |
| 2004/0076303 A1 * | 4/2004 | Vyshedskly | A61B 5/0002 381/67 |
| 2004/0157612 A1 | 8/2004 | Kim | |
| 2005/0048455 A1 | 3/2005 | Hayamizu et al. | |
| 2005/0131307 A1 | 6/2005 | Ruiter et al. | |
| 2005/0148283 A1 | 7/2005 | Schwalm | |
| 2009/0312675 A1 * | 12/2009 | Sampson | A61H 9/005 601/10 |
| 2010/0012417 A1 * | 1/2010 | Walter | B60K 28/063 180/272 |
| 2013/0071826 A1 * | 3/2013 | Johnson | G09B 23/28 434/266 |
| 2016/0262717 A1 * | 9/2016 | Smith | A61B 5/0022 |
| 2018/0158376 A1 * | 6/2018 | Tessier | A61B 5/107 |

FOREIGN PATENT DOCUMENTS

| | | |
|---|---|---|
| JP | 2005 227 534 | 8/2005 |
| WO | 2006047400 | 5/2006 |

OTHER PUBLICATIONS

Technology to Inspire: Technology Archive Electronic Stethoscope, Young Foresight: Technology to Inspire: Project Centre Report Jul. 7, 2003.

\* cited by examiner

METHOD AND APPARATUS FOR AUSCULTATION TRAINING

This application claims priority to U.S. Provisional Patent Application No. 62/296,855, filed Feb. 18, 2016, and U.S. Provisional Patent Application No. 62/308,254, filed Mar. 15, 2016, the contents of which are incorporated herein by reference.

TECHNICAL FIELD

The present invention relates to medical training devices for use in instructing medical students. More particularly, the present invention relates to an auscultation training device and a method of use therefor.

BACKGROUND

Auscultation is the act of listening to sounds within the body as a method of diagnosis. A stethoscope is an example of an auscultation device that is used in the medical field to listen to internal sounds in the human body, such as heart sounds, breathing (breath sounds), intestinal noises, blood flow through the arteries and veins, and externally produced sounds, such as percussion. Acoustic stethoscopes operate on the transmission of sound from a headpiece, via air filled tubes, to the listener's ears. The headpiece may include a diaphragm that can be placed against a human body for sensing sound. These body sounds then cause the diaphragm to vibrate, in turn creating acoustic pressure waves that travel up the hollow tubes to the listener's ears.

Forming a diagnosis of a patient using an auscultation device such as a stethoscope requires training in proper placement of the headpiece, detecting bodily sounds, and identifying abnormalities as compared to normal body sounds. Often this type of training takes advantage of simulated, or standardized, patients such as mannequins with recorded sounds being presented to the student. Other times, real human patients presenting with certain known ailments are used to train students to detect and identify body sounds in a real-time "live" environment.

In situations where a student is being trained using simulated sounds and patients, it is beneficial to use a stethoscope training aid that can recreate these simulated sounds through the earpiece of the stethoscope so the student can experience these sounds in as close to a natural condition as possible. One such device is disclosed in U.S. Pat. No. 7,645,141 to Lecat, the entire disclosure of which is fully incorporated herein by reference.

In live environments, students typically use a standard practice stethoscope to detect and identify body sounds, however, when teaching in groups, this type of environment tends to result in differing exposure between students. For example, student A may hear a body sound that is slightly different than what student B hears based on differences in placement of the stethoscope headpiece to changes in the sounds the human body makes at different times. This problem is compounded as the size of the student group increases. What is needed is a tool that allows for a blending of the live and simulated environments wherein the experience can be shared among multiple students simultaneously in order to standardize the learning experience.

SUMMARY

Provided is an auscultation training device having a stethoscope with a headpiece; at least one earpiece; tubing, wherein the tubing has a generally hollow interior; a speaker inserted into the hollow interior of the tubing, further having a 3.5 mm audio jack wherein the insertion points of the speaker forms an airtight seal with the tubing, and wherein the speaker does not obstruct the hollow interior of the tubing.

Further provided is a method of auscultation training comprising the steps of (a) providing at least one auscultation training device having a stethoscope with a headpiece; at least one earpiece; tubing, wherein the tubing has a generally hollow interior; a speaker inserted into the hollow interior of the tubing, further having a 3.5 mm audio jack; wherein the insertion points of the speaker forms an airtight seal with the tubing, and wherein the speaker does not obstruct the hollow interior of the tubing; (b) connecting the at least one auscultation training device to a remote transmitter; (c) broadcasting an audio signal from the remote transmitter to the at least one auscultation training device; and (d) playing the audio signal from the speaker.

DESCRIPTION

Figure 1:
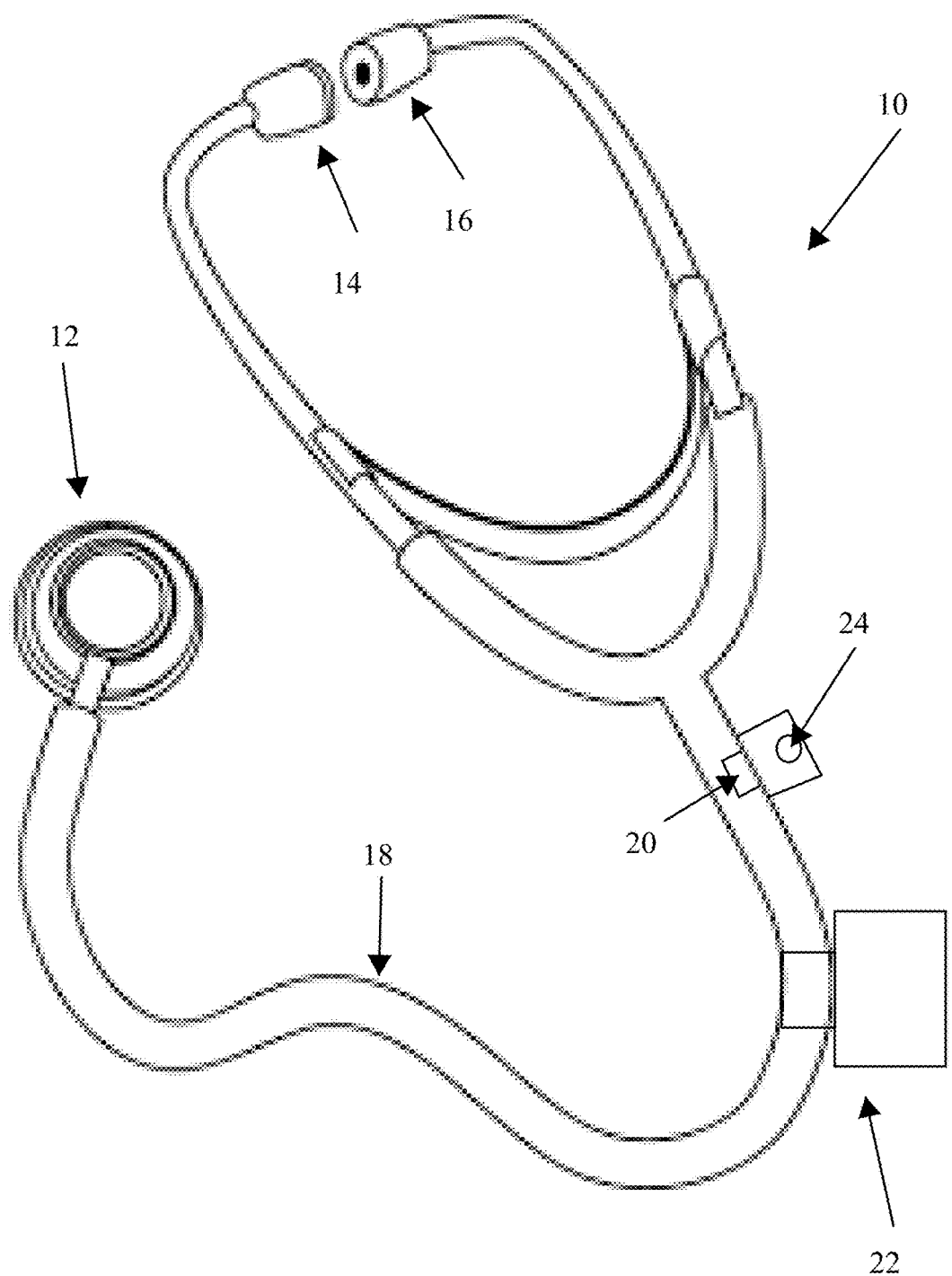
FIG. 1 is a diagram of an auscultation training device.

With reference to FIG. 1, an embodiment of an auscultation training device 10 is shown having a headpiece 12, which may be connected to a pair of earpieces 14, 16, and tubing 18, which can have a generally hollow interior. The training device 10 can also have a speaker 20 that extends into the hollow interior of the tubing 18 without fully obstructing the hollow interior of the tubing 18. The insertion point of the speaker 20 can form an airtight seal with the tubing 18 as to allow normal and natural function of the stethoscope. The training device can also have a solenoid 22 inserted within the hollow interior of the tubing 18 between the headpiece 12 and the speaker 20. The insertion point of the solenoid 22 can also form an airtight seal with the tubing 18 as to allow normal and natural function of the stethoscope. The speaker 20 can have a standard 3.5 mm audio jack 24 to allow the speaker 20 to be connected to an audio output device, including simulated patients, training mannequins, body sound simulators, mp3 players, smartphones, tablets, CD players, DVD players, or any other device capable of transmitting audio signals through a standard 3.5 mm audio connection.

According to one embodiment, the training device 10 can be used as a standard stethoscope wherein a student places the headpiece 12 on a patient to receive body sounds through normal stethoscope operation. According to this embodiment, the speaker 20 and solenoid 22 are not activated and acoustic pressure waves are free to travel through the hollow interior of the tubing 18 to the earpieces 14, 16. This arrangement allows the student to operate the training device 10 in a manner that is consistent with a live diagnosis, thereby teaching the student proper placement of the headpiece 12 and encouraging development of the student's muscle memory to aid in learning and retention of proper placement techniques.

According to one embodiment, the speaker 20 can be connected to an external audio output device and activated in a manner that would allow the student to hear body sounds generated by either the placement of the headpiece 12, the speaker 20, or both. The external audio output device can be coordinated with the placement of the headpiece 12 such that a desired body sound can be broadcast simultaneously with the placement of the headpiece 12, thereby amplifying and enhancing the live sounds detected by the headpiece 12. Alternatively, the audio output device can play audio files through the speaker 20 at a separate time, thereby allowing the student to hear a live sound separate from a simulated sound for purposes of comparison and learning.

According to one embodiment, the solenoid 22 can be activated and can mechanically block the hollow interior of the tubing 18 between the headpiece 12 and the speaker 20. This mechanical block can function to dampen or silence the transmission of sound waves from the headpiece 12. The student can then exclusively use the external audio output device and speaker 20 to generate simulated sounds without interference from live sounds generated through the headpiece 12.

According to one embodiment, the solenoid 22 can be replaced with any physical means for temporarily or permanently blocking the hollow interior of the tubes 18 to allow exclusive use of the external audio output device and speaker 20 to generate simulated sounds without interference from live sounds generated through the headpiece 12.

According to one embodiment, the speaker 20 can be connected to a wireless receiver by way of the 3.5 mm audio jack 24. The wireless receiver can be configured to receive a wireless signal that has been broadcasted from a separate device and relay the wireless signal to the speaker 20 as an audio file for playback to the student. The wireless receiver can be configured to communicate via any suitable wireless technology, including, but not limited to, Wi-Fi, Bluetooth, radio frequency (RF), infrared (IR), ZigBee, etc.

Figure 2:
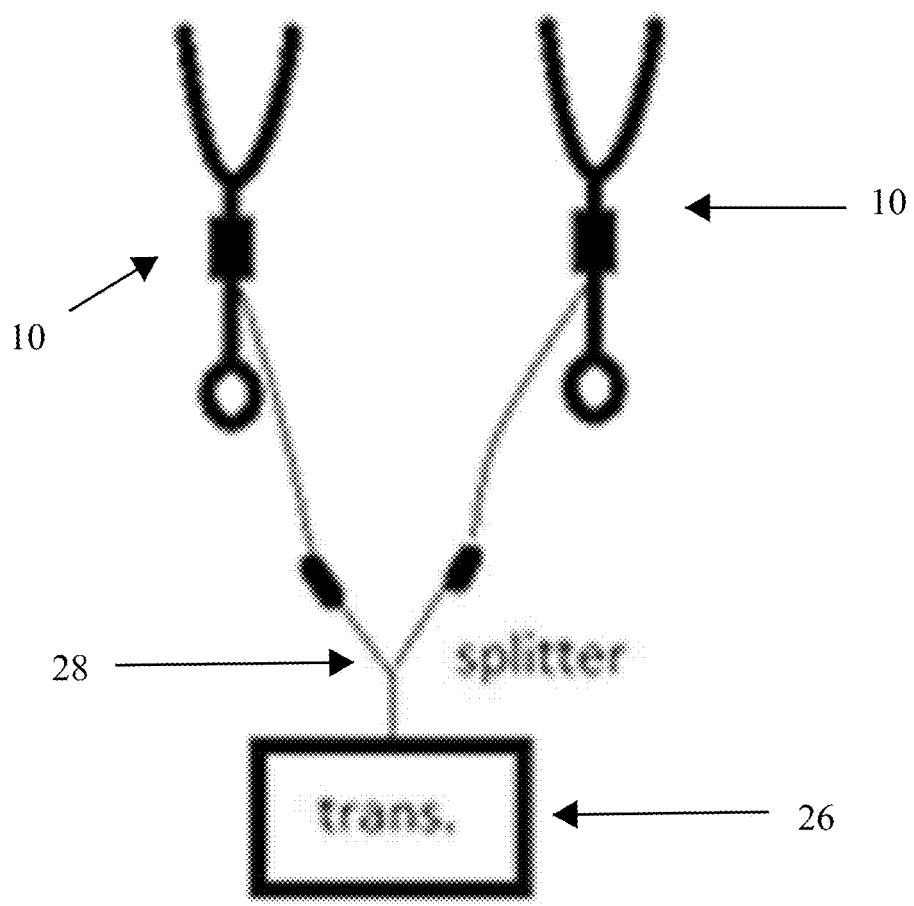
FIG. 2 is a diagram of an embodiment of the training environment.

With reference to FIG. 2, the external audio output device can consist of a transmitter 26 and a splitter 28 which can allow two of the training devices 10 to be connected simultaneously. According to one embodiment, two students can connect a training device 10 to the same audio output device allowing each student to hear the same sounds at the same time.

Figure 3:
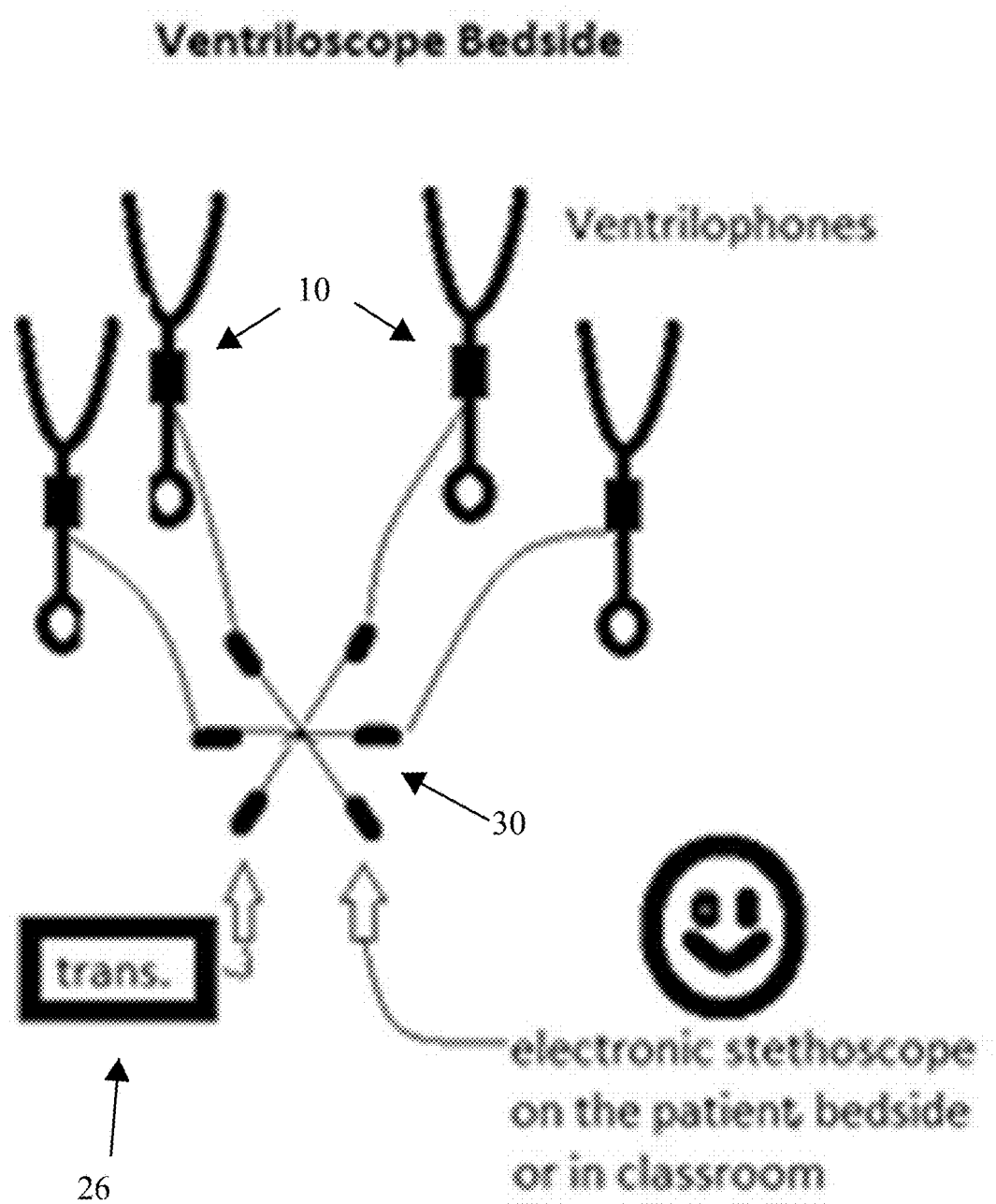
FIG. 3 is a diagram of a second embodiment of the training environment.

With reference to FIG. 3, the splitter 28 can be a multi-way splitter 30 having two or more connections. According to the embodiment shown, the multi-way splitter 30 can have six connections allowing up to five training devices 10 to connect to a single audio output device. According to one embodiment, the multi-way splitter 30 can be connected to four training devices 10, an audio output device, and an electronic stethoscope and transmitter, such as the Ventriloscope®, trademarked and owned by the present applicant and the subject matter of the '141 patent referenced herein. According to this embodiment, the training devices 10 can receive signals from either the audio output device, the electronic stethoscope, or both. This arrangement can allow multiple students to simultaneously hear sounds generated from a patient that is located remote from the students, such as in a bed in another room or in a classroom.

Figure 4:
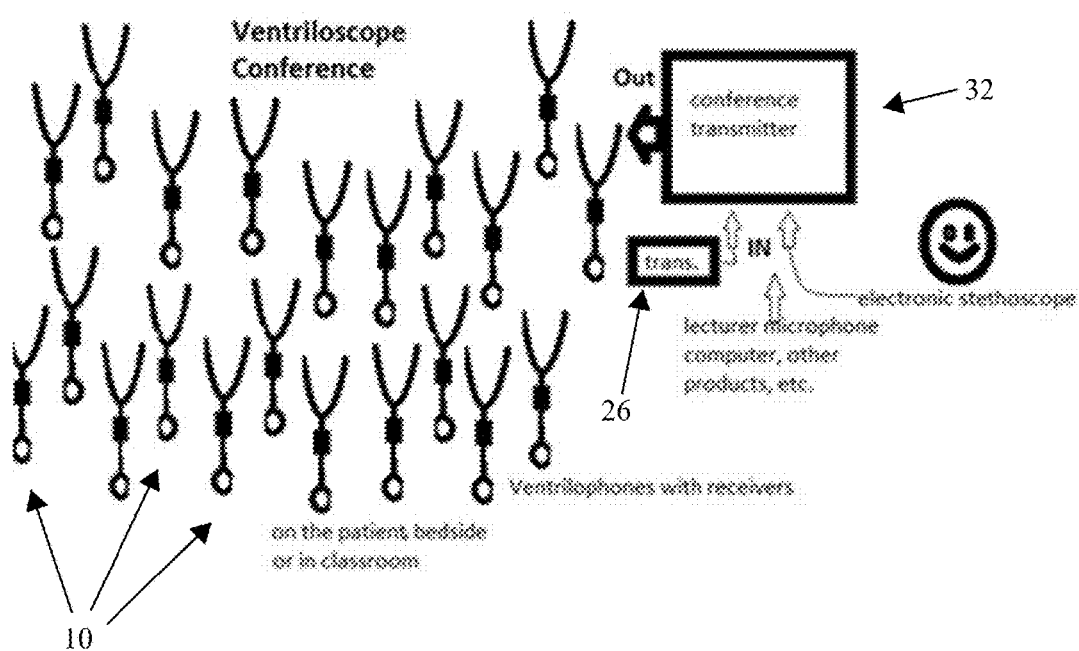
FIG. 4 is a diagram of a third embodiment of the training environment.

With reference to FIG. 4, a multitude of training devices 10 can each be connected to a wireless receiver via the 3.5 mm audio jack 24. The external audio output device can be connected to a remote transmitter 32 that is capable of receiving an audio signal from the audio device and broadcasting the signal to the multitude of training devices 10 via wireless technology. According to one embodiment, the wireless technology can be RF transmission. The remote transmitter 32 can also accept input from a lecturer, a microphone, a computer, or any other input capable of generating an audio signal. The remote transmitter 32 can also be connected to an electronic stethoscope for transmission of simulated or live patient sounds.

According to one embodiment, a patient or instructor can control which sounds the students are hearing according to the placement of a stethoscope on a patient or training simulator.

Figure 5:
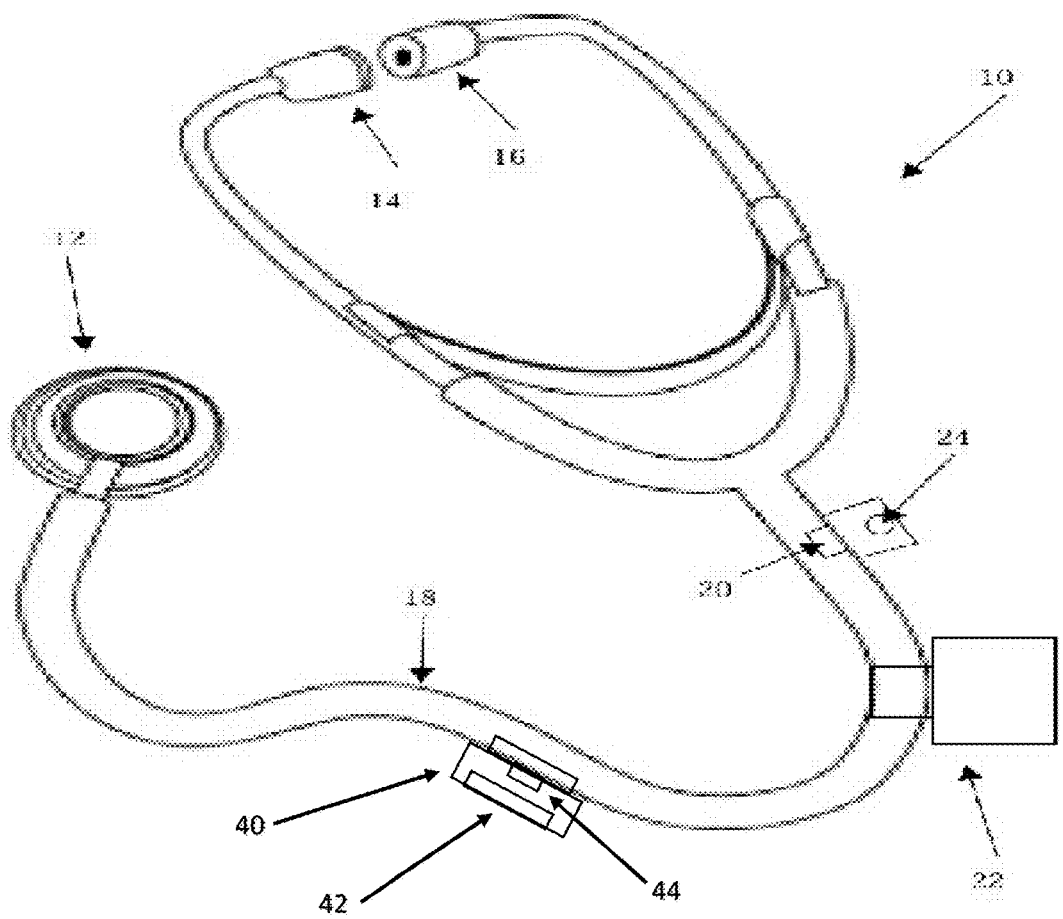
FIG. 5 is a diagram of separate embodiment of the auscultation training device.

With reference to FIG. 5, the training device 10 can include an output 40, thereby allowing the training device 10 to broadcast or record live body sounds to other training devices 10, to an external storage device such as a computer or memory card, to an external audio device, or to any other device capable of receiving and or storing an audio signal. The output 40 can be integrated into the speaker 20 or can be a separate component disposed in line with the speaker 20 and the headpiece 12. The output 40 can consist of a microphone, a recording device, a transmitter, or an audio output jack, or a combination thereof. This embodiment would allow for a training device 10 to be used as the external audio output device for other training devices 10. This would allow students to share live body sounds in real time, or to store live body sounds for future playback.

According to one embodiment, an amplification device can be connected to the training device 10 to allow for amplification of live or simulated body sounds to assist the hearing impaired.

With continued reference to FIG. 5, a light, LED, or other visual signal can be connected and synchronized to the live or simulated body sounds. By way of one example, an LED 42 and controller 44 can be connected to the output 40 of the training device 10 and synchronized so that the LED 42 illuminates simultaneously with the pulse or breathing sounds being heard through the earpieces 14, 16. This embodiment can provide visual feedback to observers who are not connected to one of the training devices 10 and can be helpful in learning to diagnose conditions where the live or simulated body sounds correlate with the timing of the pulse or breathing sounds.

According to another embodiment, the light, LED, or other visual signal can be connected to a sensor separate from the training device 10 to detect the live or simulated body sounds. By way of one example, the sensor could be an EKG lead. Other methods of detecting live or simulated body sounds, such as changing impedance, resistance, or physical movement could also be used in conjunction with or separate from the training device 10.

Although described as a medical training device, the present invention can have applicability outside the medical field in any situation where teaching using a stethoscope or listening device is used. One such example could be in the automotive industry. Thus, while the present invention has been described in connection with various illustrative embodiments, it is to be understood that other similar embodiments may be used or modifications and additions may be made to the described embodiments for performing the same function disclosed herein without deviating therefrom. Further, all embodiments disclosed are not necessarily in the alternative, as various embodiments may be combined or subtracted to provide the desired characteristics. Variations can be made by one having ordinary skill in the art without departing from the spirit and scope hereof. Therefore, the present invention should not be limited to any single embodiment, but rather construed in breadth and scope in accordance with the recitations of the appended claims.

Having thus described the invention, it is now claimed.

I claim:

1. An auscultation training device comprising:
   a stethoscope having:
      a headpiece;
      at least one earpiece;
      tubing, wherein the tubing has a hollow interior;
      a speaker inserted into the hollow interior of the tubing through an insertion point, further comprising an audio jack, wherein the insertion point of the speaker through the tubing forms an airtight seal with the tubing; and wherein the speaker does not fully obstruct the hollow interior of the tubing; and
      a solenoid inserted into the hollow interior of the tubing through an insertion point along the outer circumference and length of the tubing between the headpiece and the speaker, wherein the insertion point of the solenoid through the tubing forms an airtight seal with the tubing and wherein the solenoid is selectively operational to fully obstruct the hollow interior of the tubing when activated.

2. The auscultation training device of claim 1 further comprising an output that is able to broadcast or record live body sounds to an external storage device, said output disposed in line with the speaker and headpiece.

3. The auscultation training device of claim 2 wherein the output is integrated into the speaker and further comprises an audio output jack.

4. The auscultation training device of claim 2 wherein the output further comprises a wireless transmitter capable of transmitting an audio signal via wireless transmission technology.

5. The auscultation training device of claim 4 wherein the output further comprises a visual signal capable of providing visual feedback.

6. A method of auscultation training comprising the steps of:
   a. providing at least one auscultation training device comprising:
      a stethoscope having:
         a headpiece;
         at least one earpiece;
         tubing, wherein the tubing has a hollow interior, and;
         a speaker inserted into the hollow interior of the tubing through an insertion point, further comprising an audio jack wherein the insertion point of the speaker through the tubing forms an airtight seal with the tubing, and wherein the speaker does not fully obstruct the hollow interior of the tubing; and
         a solenoid inserted into the hollow interior of the tubing along the outer circumference and length of the tubing between the headpiece and the speaker; wherein the insertion point of the solenoid forms an airtight seal with the tubing; and wherein the solenoid is selectively operational to fully obstruct the hollow interior of the tubing when activated;
   b. connecting the at least one auscultation training device to a remote transmitter;
   c. broadcasting an audio signal from the remote transmitter to the speaker of the at least one auscultation training device; and
   d. the speaker playing the audio signal.

7. The method of claim 6 wherein the remote transmitter is connected to the audio jack of the speaker by an audio cable.

8. The method of claim 7 wherein at least two auscultation training devices are connected to the remote transmitter by a splitter and audio cables.

9. The method of claim 6 wherein the at least one auscultation training device is connected to a wireless receiver and the remote transmitter further comprises a wireless transmitter capable of wirelessly transmitting an audio signal to the wireless receiver.

10. The method of claim 9 wherein at least two auscultation training devices are connected to wireless receivers and simultaneously receive the wireless audio signal from the remote transmitter.

11. The method of claim 6 wherein the auscultation training device further comprises an output disposed in line with the speaker and headpiece, said output further comprising a wireless transmitter capable of transmitting an audio signal via wired or wireless transmission technology.

12. The method of claim 11 wherein the output is integrated into the speaker and further comprises an audio output jack.

13. The method of claim 11 wherein the remote transmitter is a different auscultation training device.

14. The method of claim 10 wherein the auscultation training device further comprises an output disposed in line with the speaker and headpiece, said output further comprising a wireless transmitter capable of transmitting an audio signal via wired or wireless transmission technology.

15. The method of claim 14 wherein the output is integrated into the speaker and further comprises an audio output jack.

16. The method of claim 14 wherein the remote transmitter is a different auscultation training device.

17. The method of claim 11 wherein the wireless transmitter of the output transmits an audio signal to a sensor separate from the auscultation training device, the sensor being connected to a visual signal capable of providing visual feedback.

18. The method of claim 14 wherein the wireless transmitter of the output transmits an audio signal to a sensor separate from the auscultation training device, the sensor being connected to a visual signal capable of providing visual feedback.

19. An auscultation training device comprising:
   a stethoscope having:
      a headpiece;
      at least one earpiece;
      tubing, wherein the tubing has a hollow interior, and;
      a speaker inserted into the hollow interior of the tubing through an insertion point along the outer circumference and length of the tubing between a first tubing end adjacent the headpiece and at least one second tubing end leading towards the at least one ear piece, further comprising an audio jack, wherein the insertion point of the speaker through the tubing forms an airtight seal with the tubing; and wherein the speaker does not fully obstruct the hollow interior of the tubing; a solenoid inserted into the hollow interior of the tubing between the headpiece and the speaker; wherein the insertion point of the solenoid forms an airtight seal with the tubing; and wherein the solenoid is selectively operational to fully obstruct the hollow interior of the tubing when activated.

20. The method of claim 17, wherein the visual signal is a light or LED that illuminates simultaneously with pulse or breathing sounds heard through the earpieces.

21. The method of claim 18, wherein the visual signal is a light or LED that illuminates simultaneously with pulse or breathing sounds heard through the earpieces.

22. The method of claim 17, wherein the sensor is an EKG lead and wherein the visual signal is a light or LED that illuminates simultaneously with readings from an EKG.

23. The method of claim 18, wherein the sensor is an EKG lead and wherein the visual signal is a light or LED that illuminates simultaneously with readings from an EKG.

24. The auscultation training device of claim 5, wherein the visual signal is a light or LED that is connected to a sensor for detecting live or simulated body sounds.

25. The auscultation training device of claim 24, wherein the sensor is an EKG lead.

\* \* \* \* \*